United States Patent
Hsiao et al.

(10) Patent No.: US 10,118,937 B1
(45) Date of Patent: Nov. 6, 2018

(54) PROCESS FOR PREPARING IXAZOMIB CITRATE AND INTERMEDIATES THEREFOR

(71) Applicant: ScinoPharm Taiwan, Ltd., Shan-Hua, Tainan (TW)

(72) Inventors: Tsung-Yu Hsiao, Tainan (TW); Jyh-Hsiung Liao, Tainan (TW)

(73) Assignee: SCINOPHARM TAIWAN, LTD., Shan-Hua, Tainan (TW)

( * ) Notice: Subject to any disclaimer, the term of this patent is extended or adjusted under 35 U.S.C. 154(b) by 0 days.

(21) Appl. No.: 15/860,949

(22) Filed: Jan. 3, 2018

(51) Int. Cl.
| | |
|---|---|
| *C07F 5/04* | (2006.01) |
| *A61K 31/166* | (2006.01) |
| *C07B 39/00* | (2006.01) |
| *C07B 43/06* | (2006.01) |
| *C07B 51/00* | (2006.01) |
| *A61P 35/00* | (2006.01) |
| *A61K 31/69* | (2006.01) |

(52) U.S. Cl.
CPC .............. *C07F 5/04* (2013.01); *A61K 31/166* (2013.01); *A61K 31/69* (2013.01); *A61P 35/00* (2018.01); *C07B 39/00* (2013.01); *C07B 43/06* (2013.01); *C07B 51/00* (2013.01)

(58) Field of Classification Search
None
See application file for complete search history.

(56) References Cited

U.S. PATENT DOCUMENTS

| | | | |
|---|---|---|---|
| 9,175,018 B2 | 11/2015 | Elliott et al. | |
| 2014/0343314 A1 | 11/2014 | Elliott et al. | |

*Primary Examiner* — Kamal A Saeed
(74) *Attorney, Agent, or Firm* — Enshan Hong; VLP Law Group LLP

(57) ABSTRACT

A process for making ixazomib citrate of formula VI comprising reacting a compound of formula V with citric acid to form ixazomib citrate of formula VI:

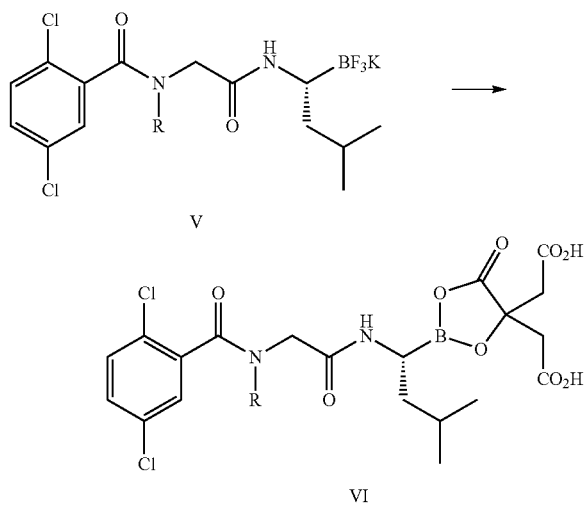

wherein R is hydrogen or an amide protecting group.

11 Claims, No Drawings

PROCESS FOR PREPARING IXAZOMIB CITRATE AND INTERMEDIATES THEREFOR

BACKGROUND OF THE INVENTION

1. Field of the Invention

The present application relates to a process for preparation of ixazomib citrate and intermediates therefor.

2. Description of the Related Art

NINLARO (ixazomib) is an antineoplastic agent. Ixazomib citrate, a prodrug, rapidly hydrolyzes under physiological conditions to its biologically active form, ixazomib. The chemical name of ixazomib citrate is 1,3,2-dioxaborolane-4,4-diacetic acid, 2-[(1R)-1-[[2-[(2,5dichlorobenzoyl)amino]acetyl]amino]-3-methylbutyl]-5-oxo-, and the structural formula is:

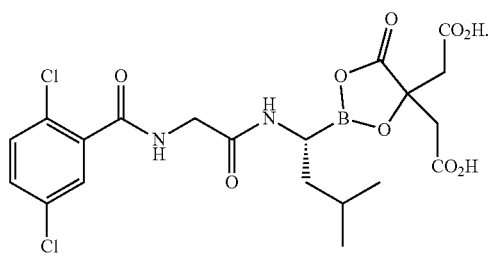 [SMILES: CC(C)C[C@H](NC(=O)CNC(=O)c1cc(Cl)ccc1Cl)B1OC(=O)C(CC(=O)O)(CC(=O)O)O1]

The molecular formula for ixazomib citrate is $C_{20}H_{23}BC_{12}N_2O_9$, and its molecular weight is 517.12.

NINLARO (ixazomib) is a proteasome inhibitor indicated in combination with lenalidomide and dexamethasone for the treatment of patients with multiple myeloma who have received at least one prior therapy.

Unlike bortezomib and carfilzomib, which are administered by injection, ixazomib citrate is the first oral PI approved by US Food and Drug Administration. In addition, ixazomib citrate is a peptide analogue that reversibly inhibits the protein proteasome subunit beta type-5 (PSMB5), which is part of the 20S proteasome complex. Moreover, ixazomib citrate has shown improvement in pharmacokinetic and pharmacodynamic parameters compared with bortezomib with a similar efficacy in controlling the myeloma growth and preventing the bone loss.

U.S. Pat. No. 9,175,018 discloses a process as shown in Scheme 1 below.

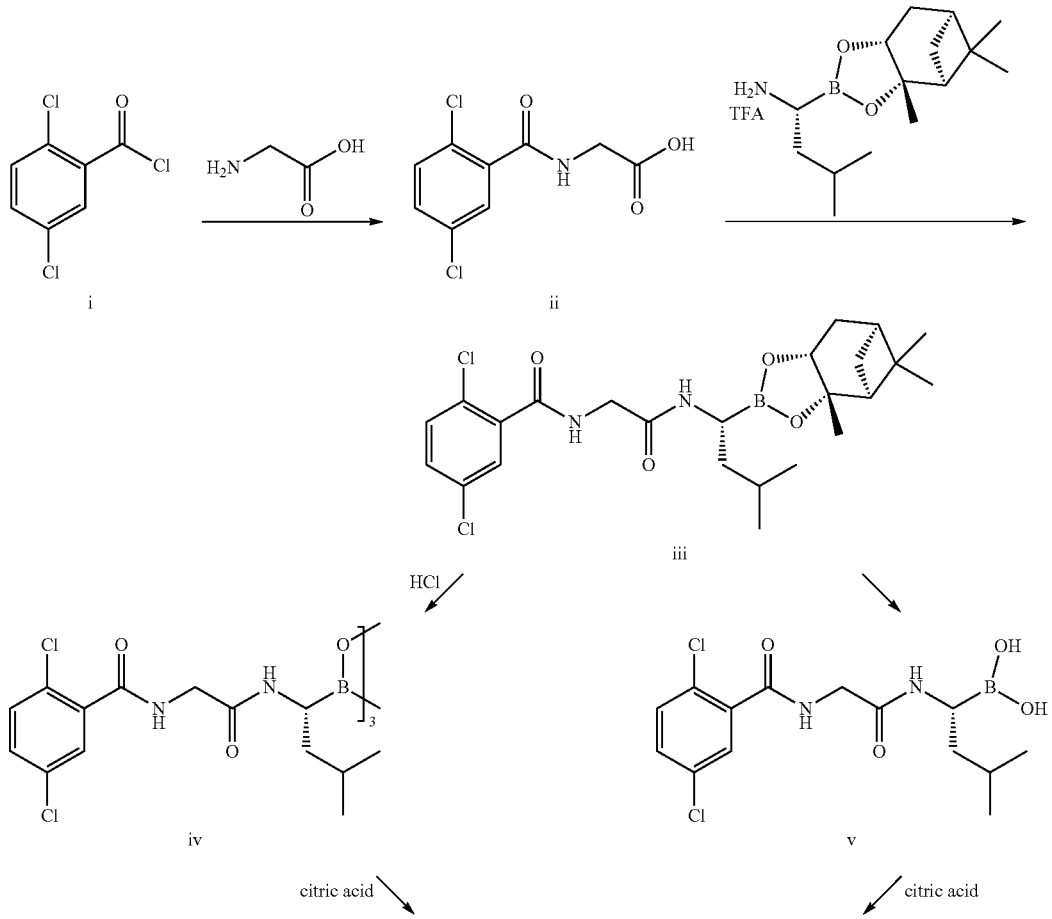

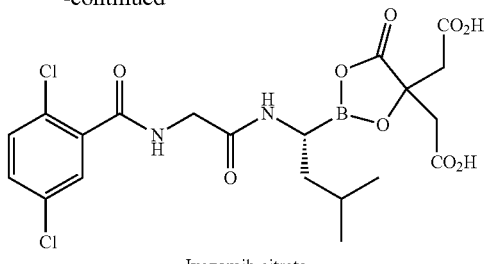

Ixazomib citrate

Specifically, U.S. Pat. No. 9,175,018 discloses that the synthesis of ixazomib citrate commences from commercially available 2,5-dichlorobenzoyl chloride i, which is reacted with glycine under basic condition to afford the corresponding dipeptide ii. Subsequent coupling the dipeptide ii with boronate trifluoroacetate salt provides the protected boronate iii. Deprotection of iii under acidic condition gives the intermediate iv or v. In the last step, the intermediate iv or v is subjected to esterification with citric acid at a temperature of 60° C. Upon cooling to ambient temperature, the final ixazomib citrate product is isolated as a white solid.

There is still a need for a convenient, low cost, and simple process of making Ixazomib citrate with a high yield and improved purity.

SUMMARY OF THE INVENTION

The present invention relates to a method for preparing Ixazomib citrate and intermediates therefor.

The first aspect of the present invention is a process for making ixazomib citrate of formula VI comprising reacting a compound of formula V with citric acid to form ixazomib citrate of formula VI:

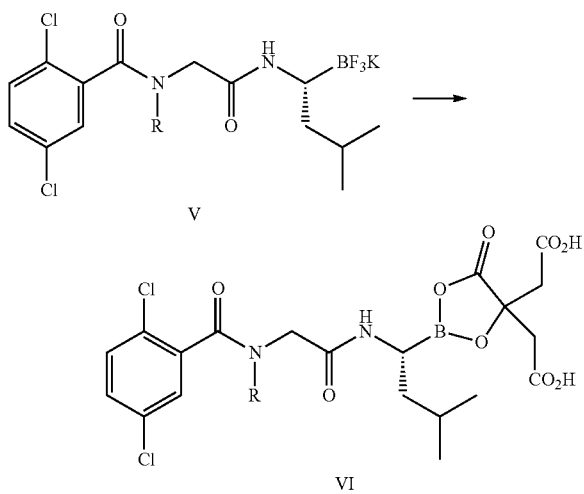

wherein R is hydrogen or an amide protecting group. The reacting step may be conducted under any appropriate conditions, for example, at a temperate from 0 to 80° C., preferably 50 to 70° C. for 1 to 30 hours, preferably 12 to 20 hours.

Preferably, the process further comprises a step of fluorinating a compound of formula IV to provide the compound of formula V:

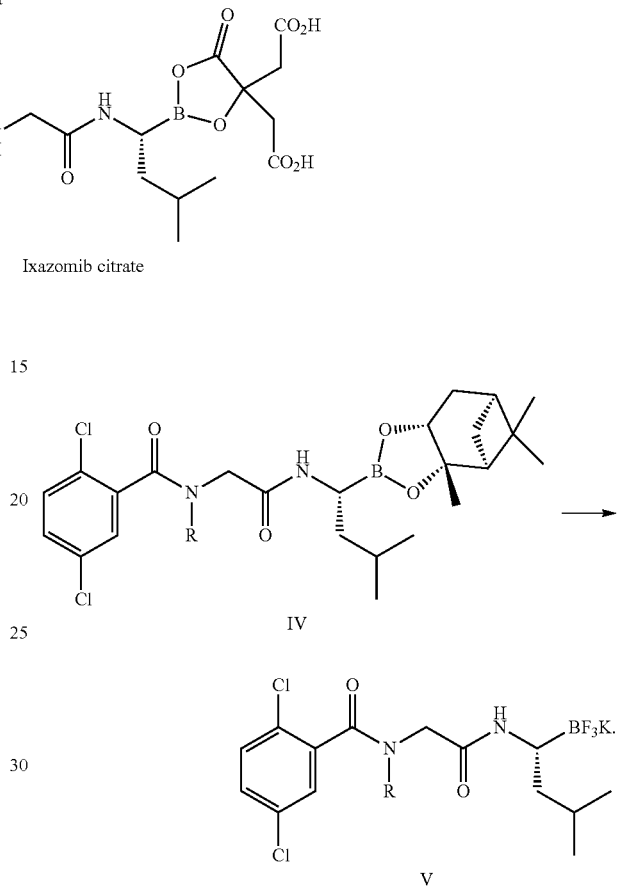

The fluorinating step may be conducted may be conducted under any appropriate conditions, for example, at a temperate from 10 to 50° C., preferably 20 to 30° C. for 10 to 30 hours, preferably 15 to 20 hours.

The amide protecting group in accordance with the present invention is preferably selected from the group consisting of trimethylsilyl, triethylsilyl, triisopropylsilyl, tert-butyldiphenylsilyl, tert-butoxycarbonyl (Boc), and 9-Fluorenylmethoxycarbonyl (Fmoc) groups.

The second aspect of the present invention is an organotrifluoroborate salt of formula V,

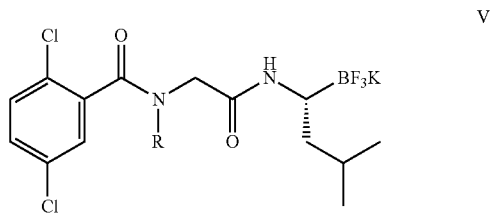

wherein R is hydrogen or an amide protecting group.

The third aspect of the present invention is a process for making a compound of formula V comprising:

fluorinating a compound of formula IV to form the compound of formula V;

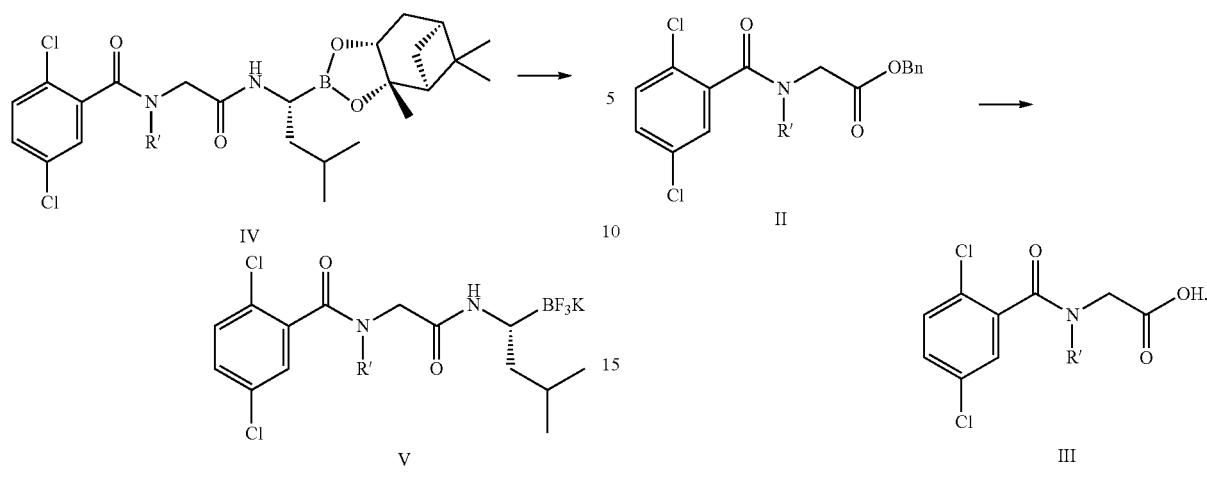

wherein R' is hydrogen or an amide protecting group. The fluorinating step may be conducted under any appropriate conditions, for example, at a temperate from 10 to 50° C., preferably 20 to 30° C. for 10 to 30 hours, preferably 15 to 20 hours.

Preferably, the process further comprises coupling a compound of formula III with a boronate trifluoroacetate salt of formula VII to provide the compound of formula IV:

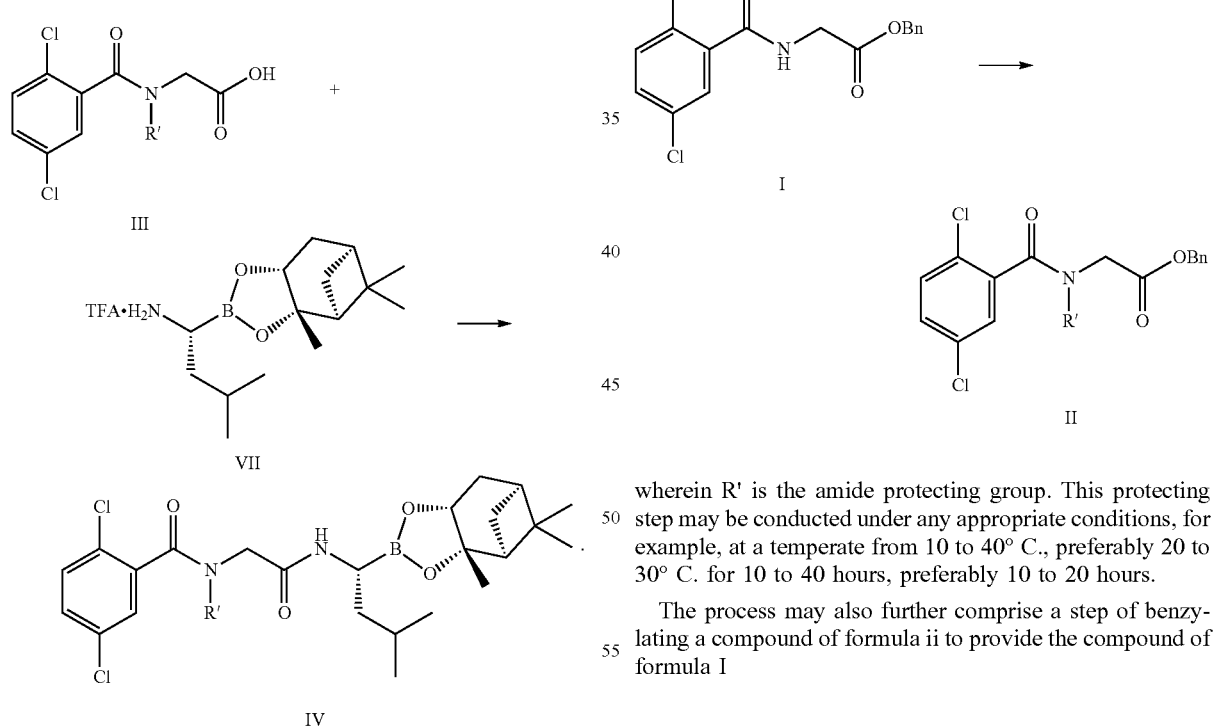

This coupling step may be conducted under any appropriate conditions, for example, at a temperate from −20 to 20° C., preferably 0 to 5° C. for 1 to 10 hours, preferably 2 to 5 hours.

Preferably, the process may further comprise reducing a compound of formula II to provide the compound of formula III:

This reducing step may be conducted under any appropriate conditions, for example, at a temperate from 0 to 40° C., preferably 20 to 30° C. for 10 to 40 hours, preferably 10 to 20 hours.

The process may further comprise protecting a compound of formula I to provide the compound of formula II:

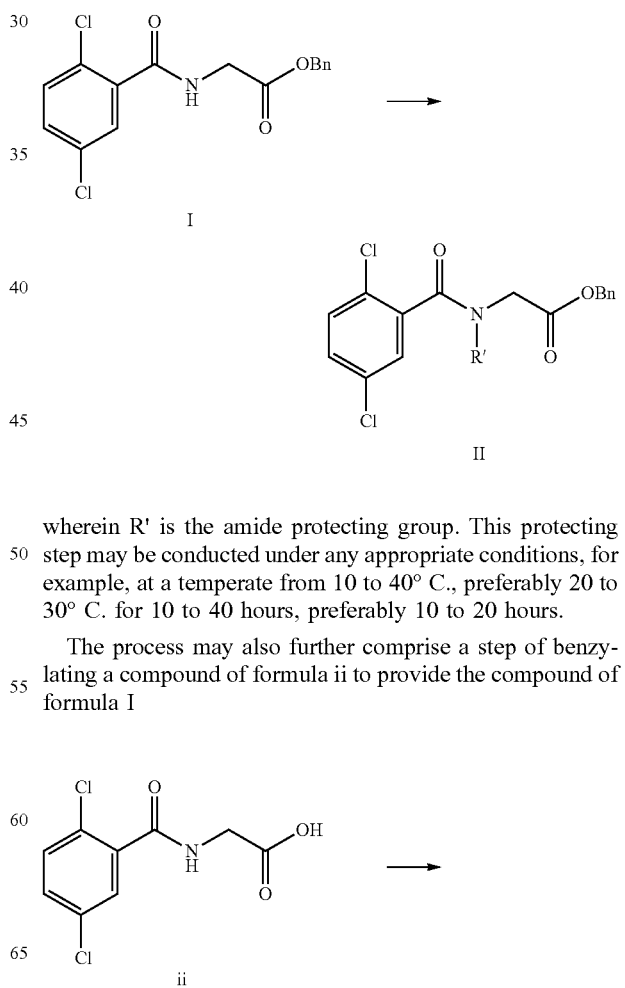

wherein R' is the amide protecting group. This protecting step may be conducted under any appropriate conditions, for example, at a temperate from 10 to 40° C., preferably 20 to 30° C. for 10 to 40 hours, preferably 10 to 20 hours.

The process may also further comprise a step of benzylating a compound of formula ii to provide the compound of formula I

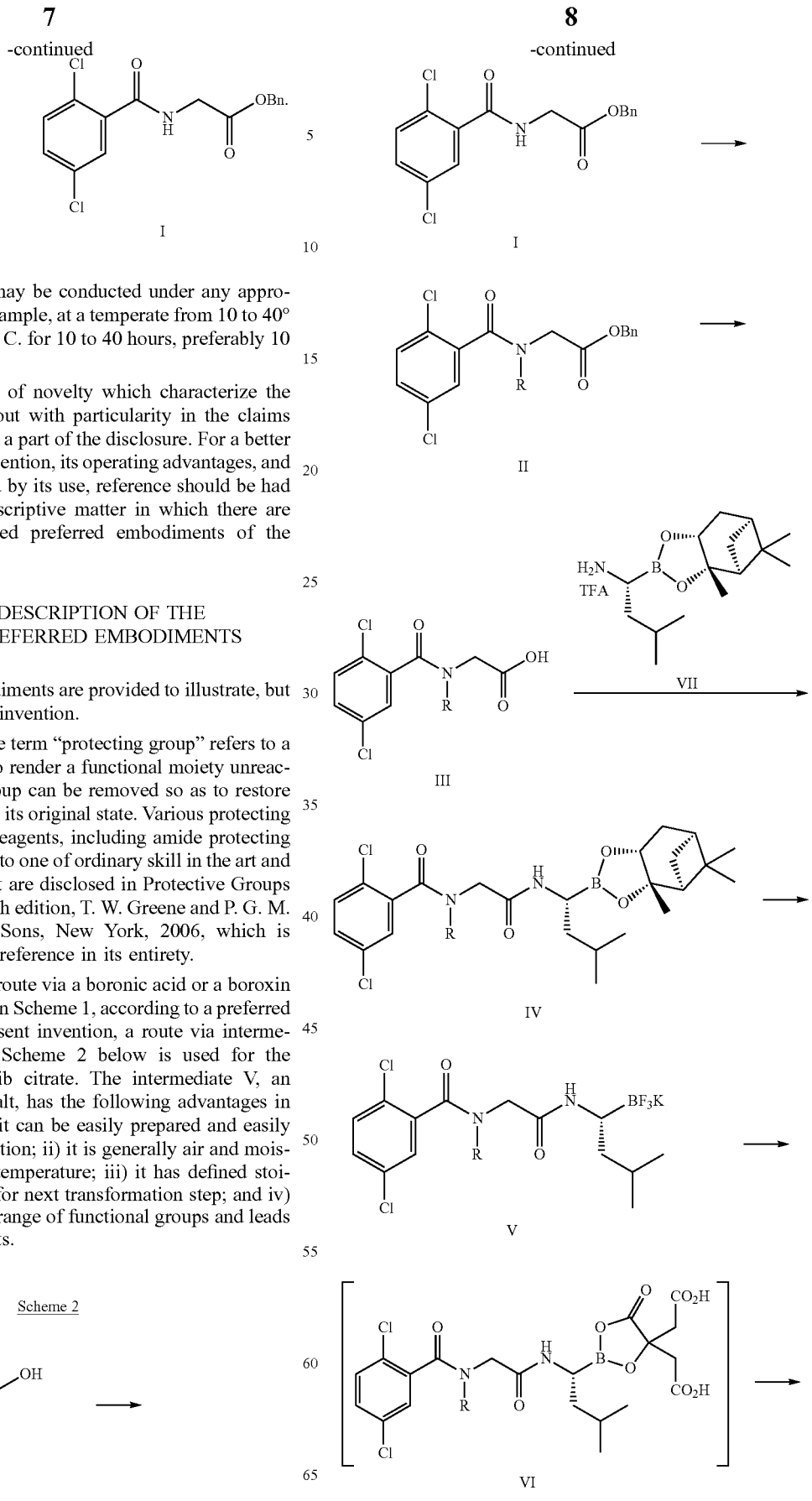

This benzylating step may be conducted under any appropriate conditions, for example, at a temperate from 10 to 40° C., preferably 20 to 30° C. for 10 to 40 hours, preferably 10 to 20 hours.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

The following embodiments are provided to illustrate, but not to limit the instant invention.

As utilized herein, the term "protecting group" refers to a moiety that is formed to render a functional moiety unreactive. The protecting group can be removed so as to restore the functional moiety to its original state. Various protecting groups and protecting reagents, including amide protecting groups, are well known to one of ordinary skill in the art and include compounds that are disclosed in Protective Groups in Organic Synthesis, 4th edition, T. W. Greene and P. G. M. Wuts, John Wiley & Sons, New York, 2006, which is incorporated herein by reference in its entirety.

Unlike the synthetic route via a boronic acid or a boroxin intermediate described in Scheme 1, according to a preferred embodiment of the present invention, a route via intermediate V as shown in Scheme 2 below is used for the preparation of ixazomib citrate. The intermediate V, an organotrifluoroborate salt, has the following advantages in synthetic chemistry: i) it can be easily prepared and easily purified by recrystallization; ii) it is generally air and moisture stable at ambient temperature; iii) it has defined stoichiometric of reagents for next transformation step; and iv) it is tolerant of a broad range of functional groups and leads to non-toxic by-products.

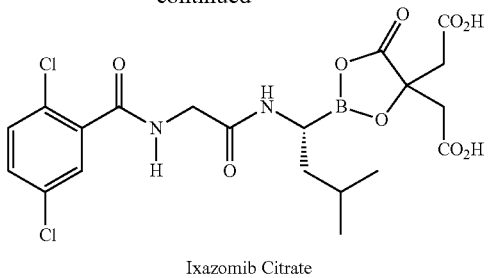

Ixazomib Citrate

As depicted in Scheme 2 above, the synthesis of ixazomib citrate in accordance with an embodiment of the present invention commences from commercially available dipeptide I, which is transformed to the acid III through the protection of I followed by reduction of the resulted benzyl ester II to the acid of III. Subsequent coupling the acid III with boronate trifluoroacetate salt provides the protected boronate IV, wherein R is an amide protecting group. Deprotection of IV via fluorinating condition provides the intermediate V which is subjected to esterification with citric acid to form the citrate VI. Deprotection of citrate VI provides ixazomib citrate isolated as a white solid.

The following Table A summarizes the advantages or characteristics of the embodiments of the instant invention compared with the processes reported in the art.

| Reference | Relevant information to this invention | Embodiments of this Invention | Differences | Advantage of the embodiments of this invention |
|---|---|---|---|---|
| U.S. Pat. No. 9,175,018 | Formation of ixazomib citrate is achieved through the condensation reaction between a boronic acid (e.g., ixazomib) and citric acid. | Formation of ixazomib citrate is achieved through the reaction between a potassium borontrifluoride and citric acid followed by a deprotection reaction. | 1. Different intermediates are employed. 2. Novel transformation is applied. | 1. Organoboranes shown in e.g., U.S. Pat. No. 9,175,018 B2 are generally not stable under atmospheric conditions, particularly alkyl- and alkynylboranes. The lack of stability of organoboranes is due to the vacant orbital on boron, which can be attacked by oxygen or water, resulting in decomposition of the reagent. Based on the embodiments of the present invention, the borontrifluoride intermediate, organotrifluoroborate salt shows exceptional stabilities toward nucleophilic compounds as well as air and moisture, which offer a stable alternative to commonly used organoboron compounds. The organotrifluoroborate salt can be stored under normal atmospheric conditions for extended periods without noticeable degradation or decomposition as compared to some of their boronic acid, boronate ester, and haloborane counterparts. 2. Generally common borontrifluorides have the limitation of being insoluble in organic media, and require polar solvents like MeCN and $H_2O$ at elevated temperatures for dissolution. Based on the embodiments of this invention, protecting group R is used in intermediate of formula V for the added advantage of being readily soluble in organic media, which |

-continued

| Reference | Relevant information to this invention | Embodiments of this Invention | Differences | Advantage of the embodiments of this invention |
|---|---|---|---|---|
| | | | | made the subsequent citrate formation easier and faster. |

The following examples are provided to further illustrate, but not to limit, certain aspects of the present invention.

EXAMPLES

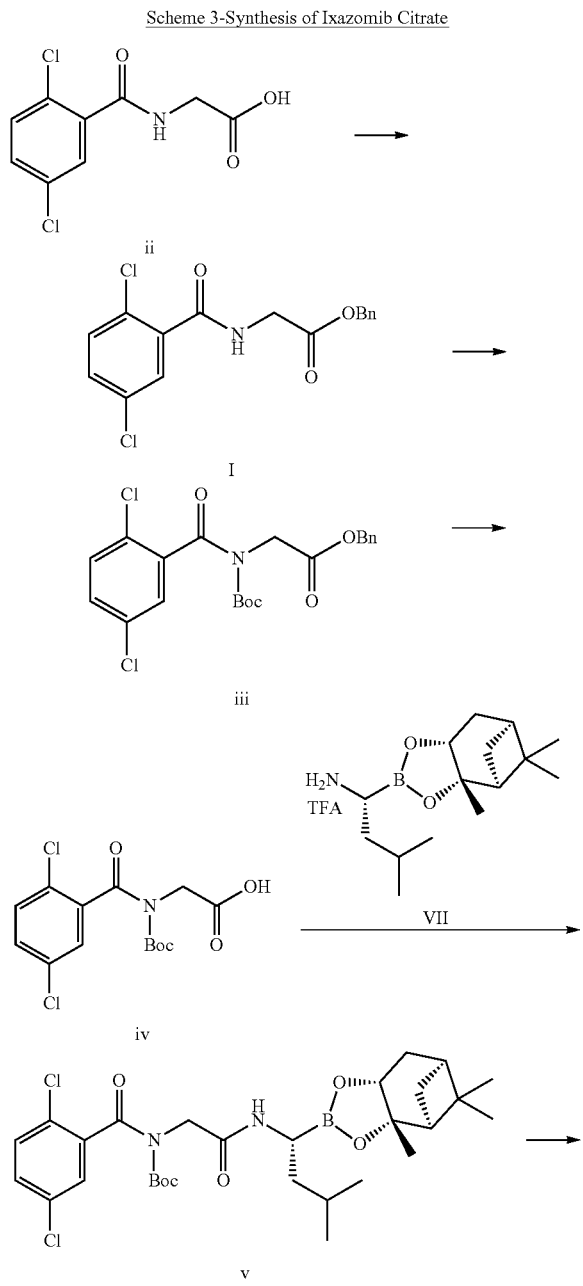

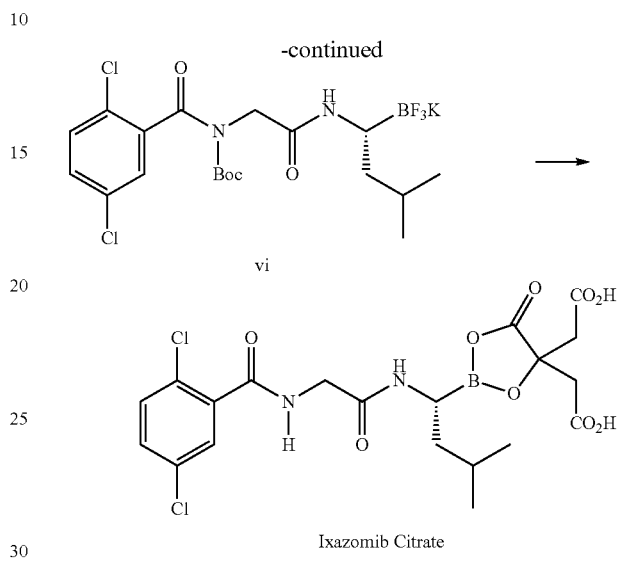

Ixazomib Citrate

Example 1

Synthesis of benzyl 2-[(2,5-dichlorobenzoyl)amino]acetate (I)

To a 250 mL, 3-necks, round-bottomed flask equipped with a magnetic stir bar (2.5 cm Teflon-coated, oval-shaped) was charged 2-[(2,5-dichlorobenzoyl)amino]acetic acid (ii) (3.00 g, 12.3 mmol, 1.00 equiv.), benzyl bromide (2.2 mL, 18 mmol, 1.50 equiv.) and acetone (30 mL), and the mixture was cooled to 0 to 5° C. Triethylamine (3.4 mL, 24 mmol, 2.00 equiv.) was added and the reaction mixture was slowly warmed to 20 to 30° C. and stirred for completion. After stirring for 20 hrs, the reaction mixture was added 1.0 N HCl aqueous solution (10 mL) followed by $H_2O$ (20 mL). The resulted suspension was filtered and the cake was washed by acetone (5.0 mL) and water (10.0 mL). The wet cake was dried at room temperature under vacuum to afford benzyl 2-[(2,5-dichlorobenzoyl)amino]acetate (I) (2.98 g) as a white solid in 73% yield.

Example 2

Synthesis of benzyl 2-[(tert-butoxycarbonyl)(2,5-dichlorobenzoyl)amino]acetate (iii)

To a 100 mL, 3-necks, round-bottomed flask equipped with a magnetic stir bar (2.5 cm Teflon-coated, oval-shaped) under $N_2$ was charged benzyl 2-[(2,5-dichlorobenzoyl)amino]acetate (I) (10.00 g, 29.57 mmol, 1.00 equiv.), DMAP (1.80 g, 14.73 mmol, 0.50 equiv.), triethylamine (5.0 mL, 35.5 mmol, 1.20 equiv.) and THF (150 mL), and the mixture was cooled to 0 to 5° C. $(Boc)_2O$ (13.0 mL, 57.0 mmol, 1.90 equiv.) was added, and the reaction mixture was slowly warmed to 20 to 30° C. and stirred for 16 hrs. The reaction mixture was cooled to 0 to 5° C. and added 0.5 N HCl aqueous solution (38 mL) followed by H$_2$O (62 mL). The mixture was added EtOAc (200 mL) and then concentrated to remove THF until the volume of the remained mixture was about 300 mL at less than 40° C. The mixture was added EtOAc (100 mL) and then concentrated to remove THF until the volume of the remained mixture was about 300 mL at less than 40° C. The resulted biphasic mixture was separated, and the organic layer was concentrated to give the crude oil which was dissolved in DCM/n-heptane (1/6, v/v) and subjected to flash column chromatography over silica gel (DCM/n-heptane, 1/6, v/v). The desired fractions were collected and concentrated to afford benzyl 2-[(tert-butoxycarbonyl)(2,5-dichlorobenzoyl)amino]acetate (iii)(13.27 g) as a brown oil in quantitative yield.

Example 3

Synthesis of [tert-Butoxycarbonyl-(2,5-dichloro-benzoyl)-amino]-acetic acid (iv)

A 25 cc 2-neck, round-bottomed flask equipped with magnetic stirring bar under N$_2$ was added benzyl 2-[(tert-butoxycarbonyl)(2,5-dichlorobenzoyl)amino]acetate (iii) (500.2 mg, 1.14 mmol, 1.00 equiv.), Methanol (5 mL) and Palladium on carbon (10%) (50.1 mg, 0.047 mmol, 0.04 equiv.) at 20 to 30° C. subsequently. The reaction flask was evacuated and purged with hydrogen (4 cycles) and the suspension was stirred at 20 to 30° C. under a balloon of H$_2$. After stirring at 20 to 30° C. for 16 hrs, the reaction mixture was filtered through celite with MeOH (5 mL) rinse. The filtrate was concentrated to give a colorless oil as the crude product of [tert-Butoxycarbonyl-(2,5-dichloro-benzoyl)-amino]-acetic acid (iv) which was used directly without further purification.

Example 4

Synthesis of 2,5-dichloro-N-(tert-butoxycarbonyl)-N-[2-({(1R)-3-methyl-1-[(3aS,4S,6S,7aR)-3a,5,5-trimethylhexahydro-4,6-methano-1,3,2-benzodioxaborol-2-yl]butyl}amino)-2-oxoethyl]benzamide (v)

A 100-mL round-bottomed flask equipped with a magnetic stir bar (1.5 cm Teflon-coated, oval-shaped) under N$_2$ was charged acid (iv) (370.1 mg, 1.063 mmol, 1.000 equiv.), a boronate trifluoroacetate salt of formula VII (420.2 mg, 1.11 mmol, 1.04 equiv.), TBTU (360.1 mg, 1.12 mmol, 1.06 equiv.) and DCM (11 mL) at 20 to 30° C. The resulting suspension was cooled to −2.5° C. and added dropwise with N,N-diisopropylethylamine (560 µL, 3.22 mmol, 3.03 equiv.). After the addition was completed, the resulting mixture was stirred at 0 to 5° C. for 2.5 hrs and stirred for completion. After the reaction was completed, the reaction was quenched with aqueous 0.5 N HCl (2 mL). The mixture was separated, and the organic layer was washed by 1.0 M NaHCO$_3$ (3 mL) followed by concentration to give a yellow liquid as the crude products. The crude products was then dissolved in DCM/n-heptane (1/1, v/v) and subjected to flash column chromatography over silica gel (EtOAc/n-heptane, 1/4, v/v). The resulting fractions were collected and concentrated to give 2,5-dichloro-N-(tert-butoxycarbonyl)-N-[2-({(1R)-3-methyl-1-[(3aS,4S,6S,7aR)-3a,5,5-trimethylhexahydro-4,6-methano-1,3,2-benzodioxaborol-2-yl]butyl}amino)-2-oxoethyl]benzamide (v) (441.2 mg) as a yellow liquid in 70% yield.

Example 5

Synthesis of potassium [(1R)-1-[[2-[tert-butoxycarbonyl-(2,5-dichlorobenzoyl)amino]acetyl]amino]-3-methyl-butyl]-trifluoro-boranuide (vi)

A 100-mL round-bottomed flask equipped with a magnetic stir bar (2.5 cm Teflon-coated, oval-shaped) under N$_2$ was charged boronate (v) (440.1 mg, 0.74 mmol, 1.00 equiv.) and methanol (10 mL) at 20 to 30° C. After stirring for 10 minutes, the resulting clear solution was added 4.5 M potassium hydrogen fluoride aqueous solution (1 mL, 4.5 mmol, 6.10 equiv.) at 20 to 30° C. and then stirred for 17 hrs. The resulting biphasic mixture was concentrated to give a wet white solid. The obtained wet cake was added n-heptane (10 mL), strongly stirred for 10 minutes and the resulted slurry was filtered. The obtained wet cake was added n-heptane (10 mL), strongly stirred for 10 minutes and the resulted slurry was filtered. The cake was washed by n-heptane (10 mL) and dried under vacuum to give the desired potassium borontrifluoride salts (vi) (376.2 mg) in 97% yield.

Example 6

Synthesis of (R)-2,2'-(2-(1-(2-(2,5-dichlorobenzamido)acetamido)-3-methylbutyl)-5-oxo-1,3,2-dioxaborolane-4,4-diyl)diacetic acid (ixazomib citrate)

A 10-mL round-bottomed flask equipped with a magnetic stirring bar (1.0 cm Teflon-coated, oval-shaped) under nitrogen was charged with potassium borontrifluoride salts (vi) (129.2 mg, 0.25 mmol, 1.000 equiv.) and ethyl acetate (3 mL). After stirring for 5 minutes at 20 to 30° C., TMSCl (400 µL, 3.15 mmol, 6.06 equiv.) was added and the mixture was stirred at 20 to 30° C. for another 40 minutes. The resulted white slurry mixture was added the solution of citric acid monohydrate (52.3 mg, 0.25 mmol, 1.00 equiv.) in ethyl acetate (3 mL) at 20 to 30° C. The slurry was then heated at 65° C. After stirring for 2 hrs, the reaction mixture was slowly cooled to 20 to 30° C. and stirred for 16 hrs. The resulting mixture was filtered under N$_2$ and the filtrate was concentrated to give yellow oil which was directly used for the next step without purification.

The obtained yellow oil was added TFA (3 mL) and stirred for 5.0 hrs. After the reaction was completed, the mixture was concentrated under reduced pressure to give the crude products. The crude product was added EtOAc (20 mL), stirred at 20 to 30° C. for 16 h, and filtered to give the desired Ixazomib citrate (83.1 mg) in 65% yield.

The invention is not limited by the embodiments described above which are presented as examples only but can be modified in various ways within the scope of protection defined by the appended patent claims.

We claim:

1. A process for making ixazomib citrate of formula VI comprising reacting a compound of formula V with citric acid to form ixazomib citrate of formula VI:

V

-continued

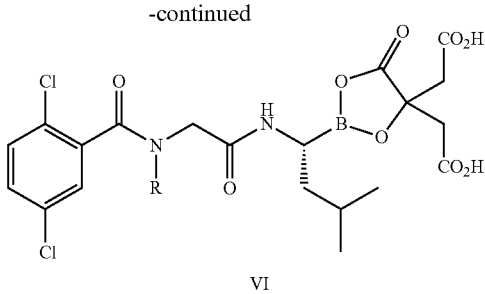

VI wherein R is hydrogen or an amide protecting group.

2. The process of claim 1 further comprising a step of fluorinating a compound of formula IV to provide the compound of formula V:

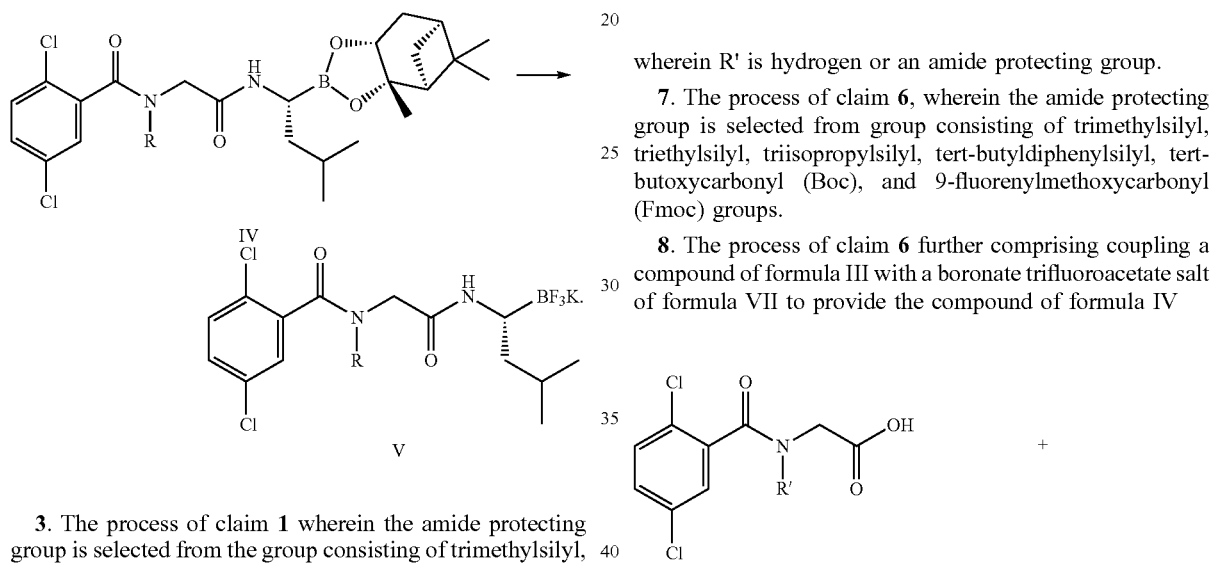

3. The process of claim 1 wherein the amide protecting group is selected from the group consisting of trimethylsilyl, triethylsilyl, triisopropylsilyl, tert-butyldiphenylsilyl, tert-butoxycarbonyl (Boc), and 9-fluorenylmethoxycarbonyl (Fmoc) groups.

4. An organotrifluoroborate salt of formula V,

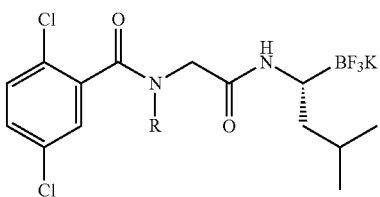

V wherein R is hydrogen or an amide protecting group.

5. The organotrifluoroborate salt of claim 4, wherein the amide protecting group is selected from the group consisting of trimethylsilyl, triethylsilyl, triisopropylsilyl, tert-butyldiphenylsilyl, tert-butoxycarbonyl (Boc), and 9-fluorenylmethoxycarbonyl (Fmoc) groups.

6. A process for making a compound of formula V comprising:
fluorinating a compound of formula IV to form the compound of formula V;

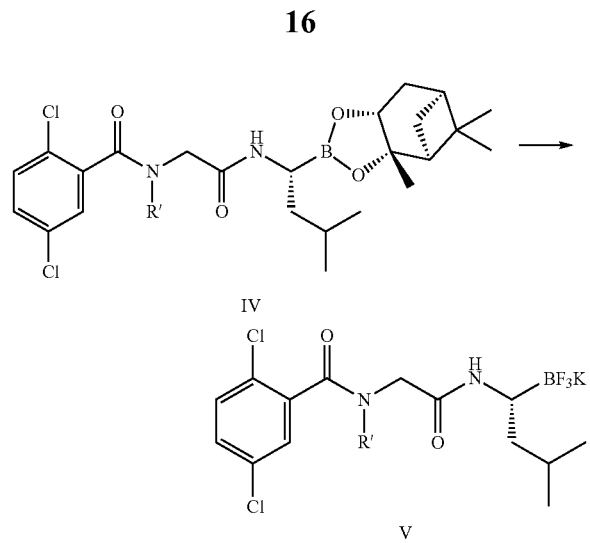

wherein R' is hydrogen or an amide protecting group.

7. The process of claim 6, wherein the amide protecting group is selected from group consisting of trimethylsilyl, triethylsilyl, triisopropylsilyl, tert-butyldiphenylsilyl, tert-butoxycarbonyl (Boc), and 9-fluorenylmethoxycarbonyl (Fmoc) groups.

8. The process of claim 6 further comprising coupling a compound of formula III with a boronate trifluoroacetate salt of formula VII to provide the compound of formula IV

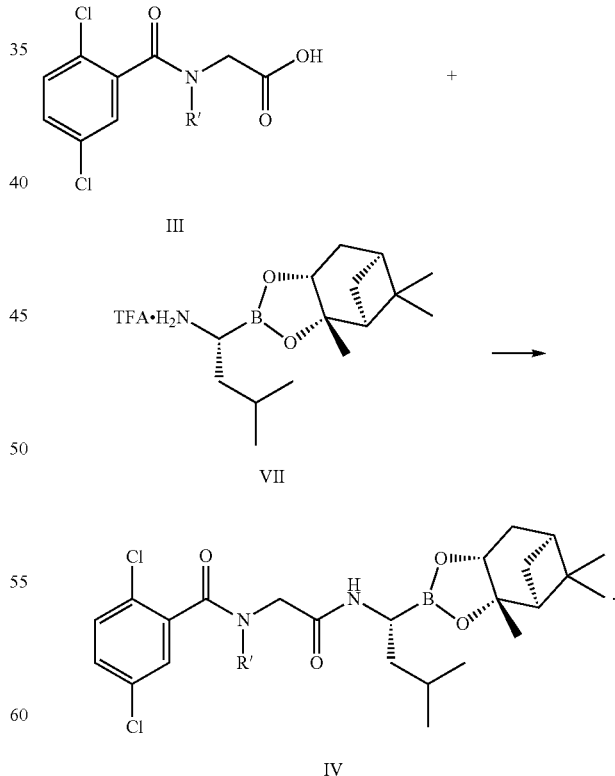

9. The process of claim 8 further comprising reducing a compound of formula II to provide the compound of formula III:

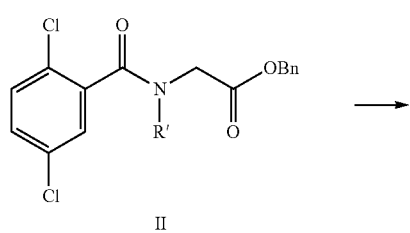
II
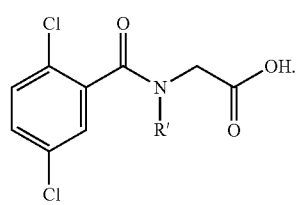
III
10. The process of claim 9 further comprising protecting a compound of formula I to provide the compound of formula II:
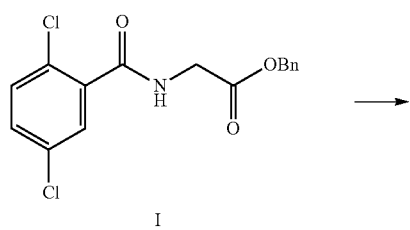
I
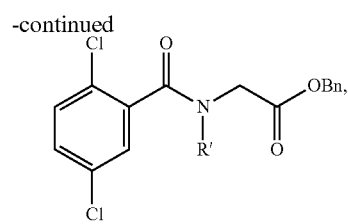
II
wherein R' is the amide protecting group.
11. The process of claim 10 further comprising a step of benzylating a compound of formula ii to provide the compound of formula I
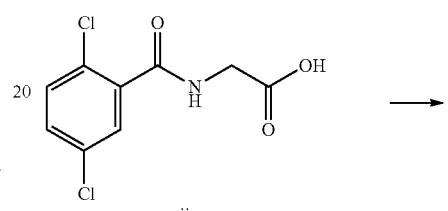
ii
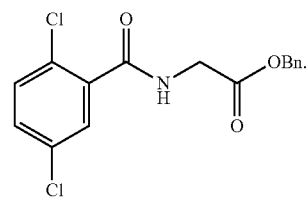
I
* * * * *